United States Patent [19]
Walter

[11] Patent Number: 4,772,265
[45] Date of Patent: Sep. 20, 1988

[54] SAFETY CATHETER

[76] Inventor: Gregory W. Walter, 59 Midwood Rd., West Babylon, N.Y. 11704

[21] Appl. No.: 26,063

[22] Filed: Mar. 16, 1987

[51] Int. Cl.⁴ ............................................. A61M 5/18
[52] U.S. Cl. .................................... 604/164; 604/168; 128/763
[58] Field of Search ................... 604/164–169, 604/162, 156, 143–144, 110, 192, 195–198, 263; 128/763–766

[56] References Cited

U.S. PATENT DOCUMENTS

| | | | |
|---|---|---|---|
| 3,463,152 | 8/1969 | Sorenson | 604/162 |
| 4,026,287 | 5/1977 | Haller | 604/196 |
| 4,160,450 | 7/1979 | Doherty | 604/164 |
| 4,392,859 | 7/1983 | Dent | 604/198 |
| 4,507,117 | 3/1985 | Vining et al. | 604/196 |
| 4,507,118 | 3/1985 | Dent | 604/198 |
| 4,542,749 | 9/1985 | Caselgrandi et al. | 604/196 |
| 4,592,744 | 6/1986 | Jagger et al. | 604/192 |
| 4,676,783 | 6/1987 | Jagger et al. | 604/162 |

Primary Examiner—Dalton L. Truluck
Assistant Examiner—Denise Whelton
Attorney, Agent, or Firm—Leonard Belkin

[57] ABSTRACT

Disposal apparatus for the safe disposal of a medicinal needle after use utilizing a container with a vacuum therein and a piston attached to one of the needles which protrudes ready for use. After use of the needle, one side of the piston is exposed to ambient pressure and the needle is retracted into the container for safe disposal.

14 Claims, 2 Drawing Sheets

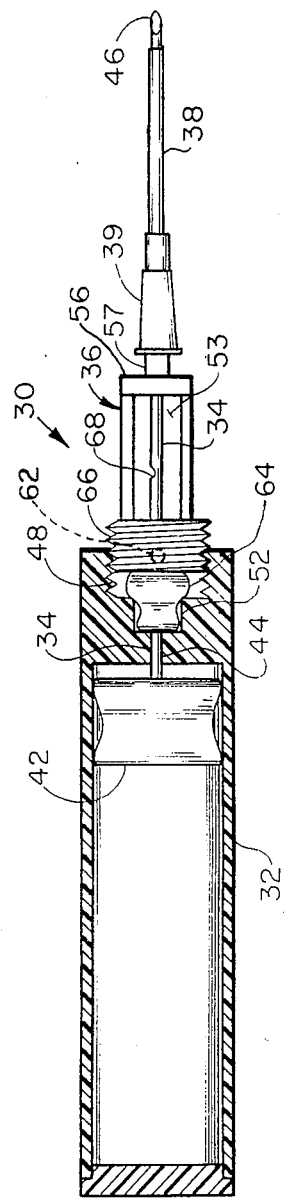
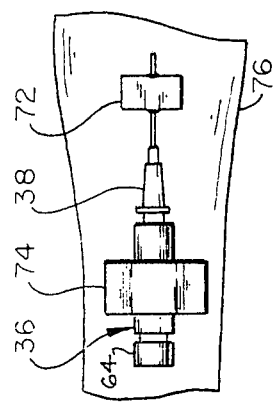
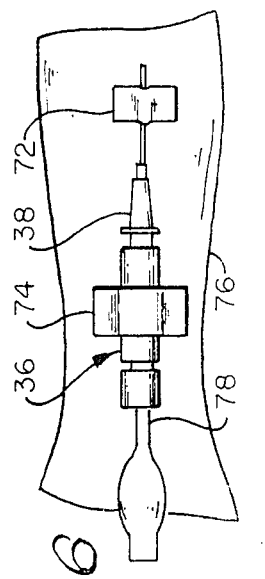
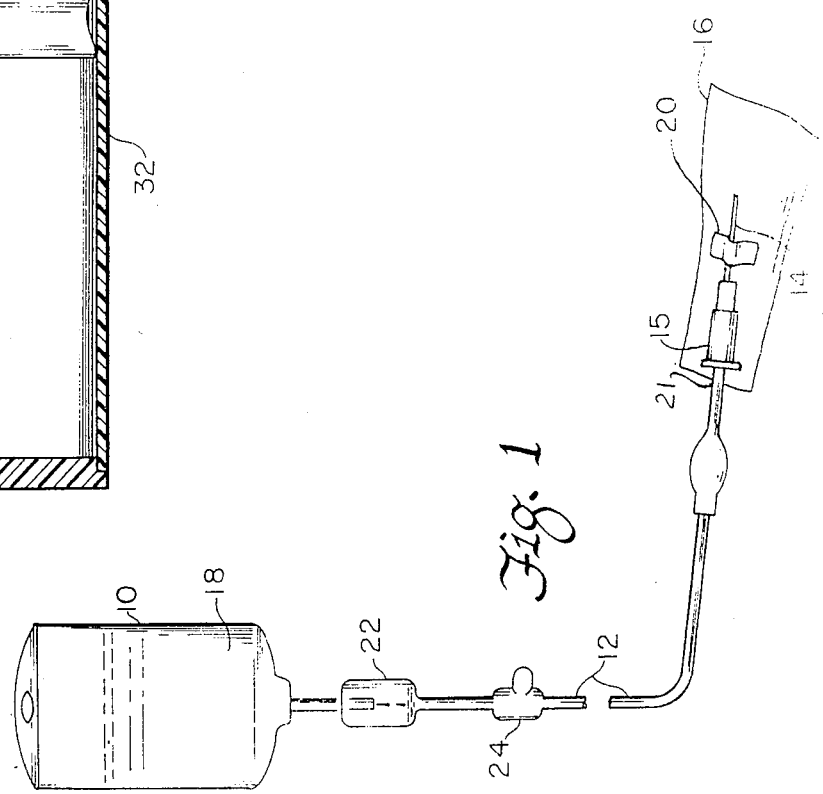

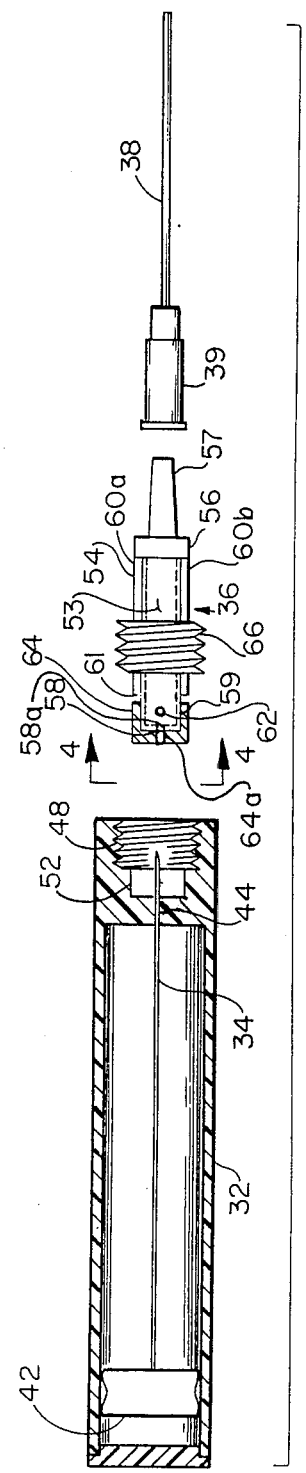
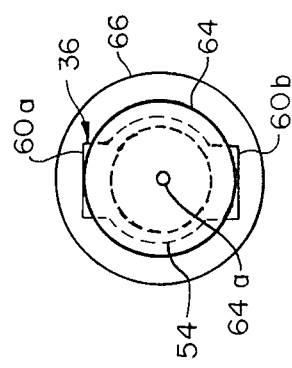
Fig. 3
Fig. 4

SAFETY CATHETER

BACKGROUND OF THE INVENTION

The present invention relates to apparatus and method for insuring the safe disposal of hypodermic needles in certain situations and for the prevention of the spread of blood borne diseases.

When a catheter is inserted into a patient, usually an arm, for the intravenous delivery of a fluid, a disposable needle passing through the catheter is utilized to make the puncture to permit entry of the tip of the catheter. The needle is then withdrawn leaving the catheter in place either for a direct hook up to the bottle of fluid to be delivered, or capped for later use. The needle, tipped with blood, is dropped into a container for disposal.

It has been found that for needles disposed of in this manner, there is a certain incidence of occurrences in which a hospital technician or other personnel receives a puncture from one of the used needles. With the developing concern over the transmission of AIDS, there is real interest in finding alternative and safer ways of disposing of such needles.

Also noted is that upon withdrawal of the needle from the catheter there is inevitably a certain amount of patient's blood spilled. This body may harbor certain viral or non-viral diseases and can be the source of exposure for other individuals caring for the patient.

In U.S. Pat. No. 3,306,290 there is taught a syringe containing a spring to retract automatically a needle.

U.S. Pat. No. 4,026,287 discloses a syringe in which the needle is retracted by having a plunger rod rotate to engage the piston attached to the needle so that the latter can be withdrawn in a positive manner.

U.S. Pat. No. 4,392,859 shows an injection gun for use with animals in which between injections the needle is put in contact with a sterilizing substance.

U.S. Pat. No. 4,507,117 discloses a syringe in which the plunger makes positive engagement with the needle piston after injection to permit withdrawal of the needle into the syringe.

U.S. Pat. No. 4,507,118 has an injection gun for use with animals which incorporates a sterilizing element to sterilize the needle between use. A spring is employed to retract the needle each time.

U.S. Pat. No. 4,542,749 teaches a syringe with automatic plunger return relying on either air compressed during injection to return the needle or a separate source of compressed fluid.

U.S. Pat. No. 4,592,744 teaches an arrangement for sheathing a needle after use in which the user of the syringe physically withdraws the latter which grasps and pulls the needle into the sheath.

The arrangements described in the patents above are either too complicated or expensive to be used as disposable items, or require that the user take positive action to effect the safe disposal of the needle, or are not applicable to the particular circumstances to which the present invention pertains.

SUMMARY OF THE INVENTION

This invention overcomes or reduces the disadvantages and drawbacks associated with previous methods and devices designed to reduce the risk of unintended puncture by disposable needles which have been used to insert a catheter in a patient and in addition provides for less exposure to disease.

Briefly described, the present invention embodies a safety catheter assembly having a vacuum chamber which acts to withdraw the needle automatically after use, not requiring that the user of the syringe take any specific extra action to effect the withdrawal or sheathing of the needle. This arrangement avoids the potential of human error and insures that in each and every case of needle use, the needle will be disposed of in a safe configuration.

In a preferred embodiment of the invention, there is provided a sealed container under a vacuum therein containing a slidable piston. A needle for making the injection to facilitate entry of the intravenous catheter is connected at its proximal end to said piston. The needle passes through said catheter to facilitate the insertion of the latter. When the needle is to be removed, a transition member connecting the container to the catheter is employed to destroy the vacuum at one end of the container on one side of the piston resulting in the latter being driven under the force of ambient pressure, retracting the needle into the container. With the needle entirely within the container, the latter can be disposed of with confidence that the needle has been rendered incapable of accidentally puncturing any personnel handling the trash for disposal.

It is thus a principal object of this invention to provide for the safe disposal of medical needles in a safe yet economical manner.

Other objects and advantages of this invention will hereinafter become obvious from the following description of a preferred embodiment of this invention.

BRIEF DESCRIPTION OF THE FIGURES

FIG. 1 is a partially schematic view of a conventional I.V. administration system in use.

FIG. 2 is a partial schematic and section view through a preferred embodiment of this invention.

FIG. 3 is an exploded view in partial section of the apparatus shown in FIG. 2 after the needle has retracted.

FIG. 4 is a view along 4—4 of FIG. 3.

FIGS. 5 and 6 show alternative arrangements for employing the invention after the needle is withdrawn.

DETAILED DESCRIPTION OF THE PREFERRED EMBODIMENTS

Referring to FIG. 1, the typical intravenous (IV) system consists of a reservoir 10 connected through tubing 12 to an intravenous catheter 14 which has been previously inserted into the arm 16 of a patient for the delivery of a parenteral liquid 18 stored in reservoir 10. Tape 20 may be employed to hold catheter 14 in place. Catheter 14 is provided with an adaptor or hub 15 to receive tubing 12 by way of a male adaptor 21.

Tubing 12 is provided with a drip chamber 22 and a flow control valve 24.

Reservoir 10 may be a rigid container which is vented so that air can replace liquid 18 as it drains out or may be a sealed collapsible bag where no venting is required.

Drip chamber 22, being of transparent material, as is understood in the art, performs the primary function of permitting the calculation of flow rate by the counting of drops, although it also may serve to remove any air bubbles which might be present in the liquid.

Flow control valve 24 permits the adjustable clamping of tube 12, and it is used to establish the drip rate at the desired value.

The conventional manner of putting intravenous catheter 14 in place as shown in FIG. 1 is to take catheter 14 which comes with a needle already passing through it with its tip exposed at the distal end of catheter 14 and make the penetration at the injection site. When blood starts dripping out of the backflow port of the needle, the needle is withdrawn from catheter 14 and adaptor 21 connected to adaptor or hub 15 at the proximal end of catheter 14. The needle is then discarded, unprotected and unsheathed, in a container or receptacle designed to receive such needles for disposition. As noted earlier, with regular frequency, unfortunately, personnel handling the exposed, discarded needles will suffer pricks from the used needles.

Also noted is that, upon withdrawing the needle from catheter 14 there is a possibility of blood flow out of hub 15 if not immediately connected to male I.V. adaptor 21.

In this invention, this hazard is avoided totally by an arrangement in which the needle once withdrawn is automatically sheathed and therefore no longer presents a hazard to any personnel. This invention incorporates features, to be described later, to prevent leakage of blood.

Refferring to FIG. 2, there is shown a safety catheter assembly 30 embodying the principles of this invention. Catheter assembly 30 consists of a cylindrical container 32, needle 34, transition member 36, and intravenous catheter 38 with an adaptor 39 to accommodate member 36. Catheter 38 is identical or similar to catheter 14 shown in FIG. 1. Assembly 30, except for a protective covering, is illustrated in FIG. 2 in the form it is assembled and delivered sterile and ready for use to install the catheter for I.V. feeding.

Cylindrical container 32 is a sealed unit containing a rubber piston 42 at one end to which is attached the proximal end of needle 34 which extends out of container 32 passing through a port 44, transition member 36, and catheter 38 terminating with its tip 46 exposed for use.

Container 32 is under a negative pressure, that is, there is a partial vacuum within.

The right end of container 32 is provided with an internally threaded recess 48 with a countersunk depression 52 to accommodate one end of transition member 36 as will be described.

Transition member 36, as also seen in FIGS. 3 and 4, consists of a sight chamber 53 formed by a transparent hollow element 54 closed at the right end with a cap 56 having a conical section 57 to enter adaptor 39 of catheter 38 and closed by a wall 58 at the left end of a hollow cylindrical section 59. Wall 58 has an opening 58a to accommodate needle 34.

Hollow element 54 is generally circular in cross section with a pair of shoulders 60a and 60b extending between cap 56 and terminating at 61 for a reason to be described, and leaving cylindrical section 59, which is circular in cross section, exposed to the left. Section 59 is provided on the side with a small air hole 62 at some intermediate point as illustrated.

Mounted on the end of and enclosing section 59 is a rubber cap 64 with an opening 64a to accommodate needle 34 designed to pass into depression 52 as seen in FIG. 2.

Needle 34 passes through port 44, opening 64a in rubber cap 64, opening 58a and sight chamber 53, and cap 56 to enter catheter 38.

A sleeve 66 threaded on the outside to engage the threads within recess 48 is fitted to and mounted on and is slidable with respect to transition member 36. When sleeve 66 is rotated into engagement with the threads in recess 48, rubber cap 59 becomes deformed or bunched up as seen in FIG. 2 acting to seal port 44 in container 32 and exposing air hole 62. There is no seal between air hole 62 and sleeve 66. The uncovering of air hole 62 keeps sight chamber 53 at ambient pressure so that when arm 26 is punctured by needle 34, there will be no air resistance to the flow back of blood into chamber 53 by way of backflow port 68 in needle 34.

It will be noted that the backflow port 68 of needle 34 is clearly visible in sight chamber 53 (see FIG. 2) so that when needle 34 enters the patient's arm to install catheter 38, blood dripping from port 68 confirms that a blood vessel has been pierced.

In the use of the apparatus shown in FIG. 2, the professional or technician uses assembly 30 in a conventional fashion to mount catheter 38 in the arm or other suitable location in the patient. When dripping blood visible in sight chamber 53 confirms that the blood vessel has been entered and the distal end of catheter 38 is located properly, then transition member 36 is separated from container 32. That is, the professional or technician grasps transition member 36 stabilizing it as he rotates container 32 counterclockwise until transition member 36 and container 32 separate. This destroys the seal around needle 34 passing through port 44 with the result that ambient pressure drives piston 42 to the left due to the vacuum on one side, until, as seen in FIG. 3, needle 34 is completely enclosed safely within container 32. At the same time, rubber cap 64 returns to its original shape as seen in FIG. 3 covering air hole 62 thereby containing the blood within sight chamber 53.

Transition member 36 remains engaged with catheter 38 while a rubber sealant closes off opening 64a in cap 64 through which needle 34 passed, preventing any leakage of blood. Such sealants are commercially available and are generally in use for sealing openings after a needle has been withdrawn.

Member 36 would remain in place mounted on catheter 38 and may be utilized in certain ways. For example, as seen in FIG. 5, catheter 38 may be retained in place by tape 72 and transition member 36 (with sleeve 66 removed) retained in place by tape 74 on arm 76 of the patient. In this way, the arrangement may be utilized for intermittent injection, that is, cap 64 and member 36 pierced with a hypodermic needle to inject a medication and periodically flushing member 36 with a solution to prevent blood clotting.

Another way to utilize transition member 36 in place is shown in FIG. 6 where a needle 78 connected to a continuously flowing solution is inserted into catheter 38 for an I.V. delivery. Member 36 of course can be removed so that an I.V. may be supplied as shown in FIG. 1.

Except for the needle, and piston 42 and cap 64 which may be made out of rubber, assembly 30 could be entirely constructed out of plastic and therefore inexpensive to manufacture.

In the arrangement described, it is seen that there has been provided an arrangement which insures that safe disposition of a needle after use without requiring extra specific steps to be taken by the user of the equipment.

While only a preferred embodiment of the invention has been described, it is understood that many changes are possible without departing from the principles of this invention as defined in the claims which follow.

What is claimed is:

1. Apparatus for the safe disposal of a medicinal needle comprising:
   a. sealed container means under a vacuum therein containing slidable piston means;
   b. said needle attached at one end to said piston means and extending out of said container means;
   c. hollow catheter means for receiving said needle for the penetration of a blood vessel of a patient to facilitate insertion of the distal end of said catheter means;
   d. transition means for sealing said container means where said needle extends out of said container means and for engaging the proximal end of said hollow catheter means whereby said needle passes through said transition means to enter said catheter means through said proximal end;
   e. said transition means including means upon separation of said transition means from said container means to expose one side of said piston means to ambient pressure thereby to effect movement of said piston means within said container means to retract said neelde into said container means whereby said needle is safely enclosed for disposal after use.

2. The apparatus of claim 1 in which said needle is provided with a backflow port, and said transition means includes a sight chamber wherein said backflow port is visible.

3. The apparatus of claim 1 wherein said transition means is releasably engaged to said catheter means.

4. The apparatus of claim 1 in which said transition means includes means to close off the proximal end of said catheter means after said container means is detached therefrom and said needle is retracted.

5. The apparatus of claim 1 in which said container means with needle, transition means, and catheter means come assembled as a sterile unit available for the insertion of said catheter into said patient.

6. The apparatus of claim 1 in which said container means includes a threaded recess through which said needle passes, and said transition means includes means extending into said recess for receiving said needle and further means threaded into said recess for effecting the seal between said needle and said container means.

7. The apparatus of claim 6 in which said needle is provided with a backflow port, and said transition means includes a sight chamber wherein said backflow port is visible, said sight chamber having an air opening permitting ambient pressure within said sight chamber while said transition means includes means for being threadably engaged to said container means.

8. The apparatus of claim 7 wherein said transition means includes means to shut said air opening when said transition means is disengaged from said container means.

9. A sterile and disposable apparatus for the safe disposition of a medicinal needle used in connection with a hollow catheter for insertion of the latter into the blood vessel of a patient, said apparatus comprising an assembly of:
   a. container means having means supporting within said container means the proximal end of said needle protruding from one end of said container means;
   b. said hollow catheter outside of and including means for releasably connecting said catheter to said container means for receiving said needle with the tip of the latter protruding from the distal end of said catheter and ready for use;
   c. transition means for joining and being releasably engaged to both said catheter and container means and through which said needle passes; and
   d. retracting means within said container means which, upon disengagement of said transition means from said container means, causes said needle to retract into said container means for disposal with the needle safely contained therein, leaving said catheter means available to remain inserted into said blood vessel, said transition means remaining releasably engaged to and sealing the opening into the proximal end of said catheter.

10. The apparatus of claim 9 in which said needle has a backflow port and said transition means includes a sight chamber for viewing said port.

11. The apparatus of claim 10 wherein said transition means includes means to maintain ambient pressure within said sight chamber when attached to said container means and to seal said sight chamber against leakage of blood when said transition means is released from said container means.

12. The apparatus of claim 11 wherein said retracting means comprises a vacuum within said container means and a piston at one end thereof attached to the proximal end of said needle, said transition means having means upon being disengaged from said container means to expose one side of said piston to permit ambient pressure to drive said piston in the direction of pulling said needle into said container means.

13. The method of safely disposing of a medicinal needle comprising the steps of attaching the proximal end of said needle to a piston within a sealed container under vacuum, said needle extending out of said container prepared for use, and destroying the seal around said needle in said container after use of said needle thereby exposing one side of said piston to ambient pressure causing movement of said piston within said container and retraction of said needle into said container whereby said needle is safely sheathed.

14. The method of claim 13 wherein said needle prior to use passes through transition means, said seal being destroyed by the step of separating said transition means from said container after use of said needle.

* * * * *